United States Patent [19]

Elliott et al.

[11] Patent Number: 4,614,798

[45] Date of Patent: Sep. 30, 1986

[54] PROCESS FOR THE PRODUCTION OF XYLAZINE

[75] Inventors: Richard L. Elliott, Kansas City; Paul H. Ruehle, Gladstone, both of Mo.

[73] Assignee: Vetamix, Shenandoah, Iowa

[21] Appl. No.: 721,362

[22] Filed: Apr. 9, 1985

[51] Int. Cl.$^4$ .................. C07D 279/04; C07C 161/02
[52] U.S. Cl. ......................................... 544/53; 558/18
[58] Field of Search .......................... 260/454; 544/53; 558/18

[56] References Cited

U.S. PATENT DOCUMENTS 3,235,550  2/1966  Behner et al. ..................... 544/53

OTHER PUBLICATIONS

Shahak et al., J. Am. Chem. Soc., 95, 3440 (1973).

Jen et al., J. Med. Chem., 18, 99 (1975).

Primary Examiner—Henry R. Jiles
Assistant Examiner—Robert C. Whittenbaugh
Attorney, Agent, or Firm—Larson and Taylor

[57] ABSTRACT

In the preparation of 2,6-dimethylphenylisothiocyanate by reacting N-(2,6-dimethylphenyl)acetamide with sodium hydride in an organic solvent to form the corresponding anion of said amide, then reacting carbon disulfide with said anion to form said 2,6-dimethylphenylisothiocyanate, unexpectedly high yields are obtained by using as the organic solvent tetrahydrofuran or a mixture of N,N-dimethylacetamide and toluene. 2,6-Dimethylphenylisothiocyanate is an intermediate in the preparation of xylazine useful, for instance, as a sedative, an analgesic and muscle relaxant.

8 Claims, No Drawings

PROCESS FOR THE PRODUCTION OF XYLAZINE

BACKGROUND OF THE INVENTION

1. Field of the Invention

This invention relates to an improved process for the preparation of xylazine. More particularly, the invention is directed to an improvement in the production of 2,6-dimethylphenylisothiocyanate an intermediate from which xylazine is prepared.

2. Description of the Prior Art

Xylazine, the well known sedative, analgesic, and muscle relaxant, has been produced by various alternate synthesis. One common synthesis can be summarized as follows:

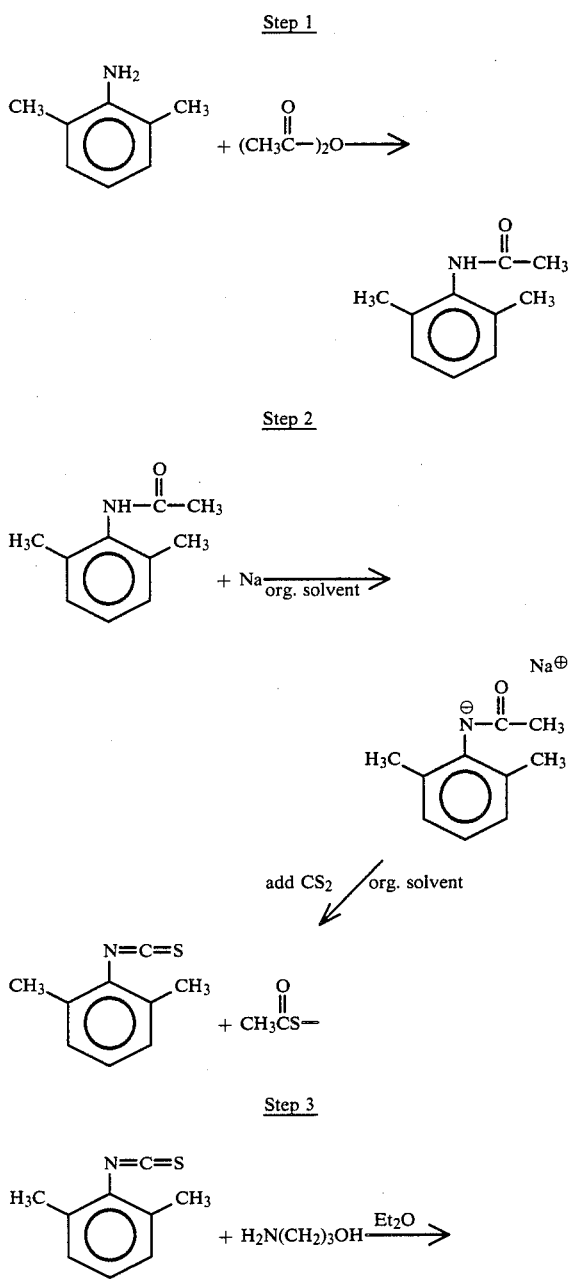

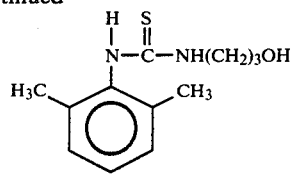

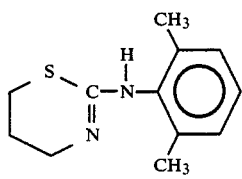

In step 2 of this synthesis the organic solvent of choice in converting the amide first to the corresponding anion by the sodium hydride and then to the isothiocyanate by the addition to carbon disulfide is a 1:1 mixture of N,N-dimethylacetamide and benzene. See (a) I. Shahak and Y. Sasson, *J. Am. Chem. Soc.*, 95, 3440 (1973). Unfortunately, even under the conditions considered optimum by the prior art, the highest yields of 2,6-dimethylisothiocyanate achievable have been on the order of 74-76 percent.

OBJECTS OF THE INVENTION

Accordingly, it is an object of the invention to provide a process which produces improved yields of 2,6-dimethylisothiocyanate and consequently improved yields of xylazine.

Another object of the invention is to provide a process improved in the amounts of solvent that can be recovered after step 2 of the synthesis.

SUMMARY OF THE INVENTION

These and other objects of the invention are obtained by an improvement in the preparation of 2,6-dimethylphenylisothiocyanate by reacting N-(2,6-dimethylphenyl)acetamide with sodium hydride in an organic solvent to form the corresponding anion of said amide, reacting carbon disulfide with said anion to form said 2,6-dimethylphenylisothiocyanate, which improvement comprises using as the organic solvent an organic solvent selected from the group consisting of tetrahydrofuran and a mixture of N,N-dimethylacetamide and toluene in a weight ratio of 1:4 to 4:1.

It now has unexpectedly been found that when either tetrahydrofuran or the mixture of N,N-dimethylacetamide and toluene is employed as the solvent system in the reaction of N-(2,6-dimethylphenyl)-acetamide with sodium hydride to form the corresponding anion followed by the addition of carbon disulfide for reaction with the anion, there results a yield of 2,6-dimethylisothiocyanate well in excess of 80 percent which has never been able to be obtained with the solvent system of choice, i.e. a 1:1 mixture of N,N-dimethylacetamide and benzene even at extended reaction periods. The results are particularly surprising since the N,N-dimethylacetamide/toluene solvent system of the invention differs from the prior art solvent system, by the substitution of toluene for benzene.

Selection of tetrahydrofuran as the solvent system, moreover, provides the added advantage over the N,N- dimethylacetamide/toluene solvent system in that it can all be recovered for reuse by simple reduced pressure distillation prior to recovery of the desired production. This is not possible with the dimethylacetamide/toluene solvent system and results in larger volumes of waste solvent mixture. If solvent recovery is not a major concern, however, the N,N-dimethylacetamide/toluene solvent system does have an advantage over tetrahydrofuran in that it produces greater than 80 percent yields of desired product at a significantly faster rate.

In another aspect of the invention, the above-described synthesis of 2,6-dimethylphenylisothiocyanate is employed as an intermediate reaction in the overall synthesis of xylazine which comprises, (i) reacting 2,6-dimethylaniline with acetic anhydride to form N-(2,6-dimethylphenyl) acetamide, (ii) reacting said N-(2,6-dimethylphenyl)acetamide with sodium hydride in an organic solvent to form the corresponding anion of said amide and reacting carbon disulfide with said anion to form 2,6-dimethylphenylisothiocyanate;

(iii) reacting said 2,6-dimethylphenylisothiocyanate with 3-amino-1-propanol in a polar solvent to form the corresponding thiourea and adding concentrated hydrochloric to said thiourea and refluxing to form xylazine, the improvement comprising using as the organic solvent in reaction step (ii) an organic solvent selected from the group consisting of tetrahydrofuran and a mixture of N,N-dimethyacetamide and toluene in a weight ratio of 1:4 to 4:1.

DETAILED DESCRIPTION OF THE INVENTION

Preparation of N-(2,6-Dimethylphenyl)acetamide

Preparation of N-(2,6-dimethylphenyl)acetamide is prepared by the reaction of 2,6-dimethylaniline and acetic acid anhydride according to conventional procedures described, for instance, in T. Jen, H. Van Haven, W. Graves, R. A. McLean, and B. Loev, *J. Med. Chem.*, 18, 99 (1975), hereby incorporated by reference. In brief, a molar excess of acetic anhydride is added dropwise to a solution of 2,6-dimethylaniline in a polar solvent such as tetrahydrofuran (THF). Upon completion of the exothermic reaction, the reaction mixture is stirred and poured into ice water. The precipitate that forms is collected and the desired N-(2,6-dimethylphenyl)acetamide product is recovered by filtration and recrystallation.

Preparation of 2,6-Dimethylphenylisothiocyanate (1) The general synthesis by which 2,6-dimethylphenylisothiocyanate may be prepared from N-(2,6-dimethylphenyl)acetamide, except for the solvent systems of the invention, is also well known. See, for example, the general synthesis reported in I. Shahak and Y. Sasson, *J. Am. Chem. Soc.*, supra.

(2) Briefly, this preparation involves first adding the acetamide to a suspension of sodium hydride in an organic solvent, preferably a N,N-dimethylacetamide/benzene solvent system. The cessation of hydrogen indicates completion of the reaction after which the reaction mixture is cooled and carbon disulfide added slowly. When tetrahydrofuran is the solvent employed, a reaction time of approximately 1.5 hours is required to provide yields in excess of 80 percent while when a mixture of N,N-dimethylacetamide/toluene is used, yields in excess of 80 percent are obtained in approximately 20 minutes.

The desired isothiocyanate product may be recovered in any suitable fashion such as by pouring the reaction mixture into water to form an organic phase and water phase and then distilling the organic phase.

Preparation of Xylazine

The preparation of xylazine from 2,6-dimethylphenylisothiocyanate is well documented as can be seen from the synthesis described in U.S. Pat. No. 3,235,550 to O. Behner et al; German Pat. No. 1,173,475 (July 9, 1964); and Belgium Pat. No. 634,552 (Jan. 6, 1964), all incorporated herein by reference. This synthesis comprises simply reacting the 2,6-dimethylphenylisothiocyanate with 3-amino-1-propanol in a polar solvent such as ether and the mixture refluxed for approximately 0.5 hr to form the thiourea:

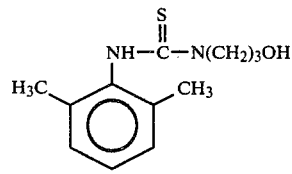

The solvent is then removed and concentrated hydrochloric acid added with continued refluxing for another 0.5 hour. The reaction mixture is cooled, treated with water, filtered and the filtrate made basic to form a precipitate which is recrystallized to give the xylazine.

The following examples are included to further illustrate the present invention.

EXAMPLE I

Xylazine was prepared by a synthesis that comprised the following steps 1, 2 and 3:

Step 1: N—(2,6-Dimethylphenyl)acetamide

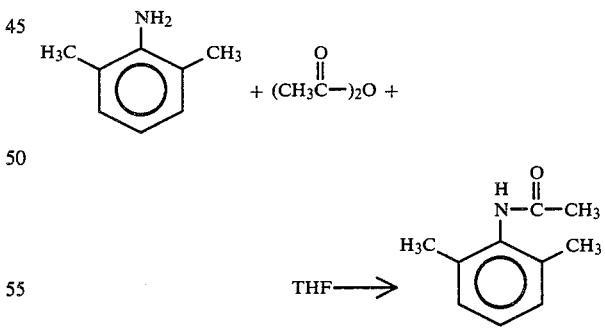

To a solution of 2,6-dimethylaniline (100 g. 0.826 mole) in 100 ml of tetrahydrofuran was added acetic anhydride (204 g, 2.0 moles) dropwise over a 1.5 hr period. After a brief induction period, the reaction became exothermic, and at the end of the addition the temperature of the reaction mixture was 60° C. The mixture was stirred 0.5 hr and poured into ice water. The precipitate was collected by filtration, and recrystallization from 300 ml of ethanol gave 113.8 g (84%) of product, m.p. 179°–181° C. (lit. m.p. 180°–181° C.).

Step 2: 2,6-Dimethylphenylisothiocyanate

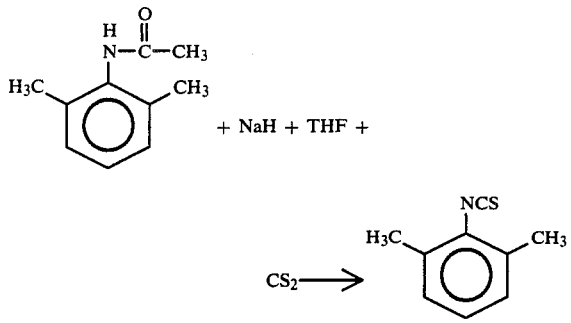

A stirred mixture of sodium hydride (2.0 g of a 60% dispersion, 0.05 mole) in 80 ml of tetrahydrofuran was warmed to 35° C. and N-(2,6-dimethylphenyl)acetamide (8.2 g, 0.05 mole) was added portionwise. When the hydrogen evolution ceased, the clear reaction mixture was cooled in an ice bath and carbon disulfide (5.9 g, 0.075 mole) was added dropwise. The reaction mixture was allowed to warm to ambient temperature with stirring for 1.5 hr. The resulting mixture was poured into water and extracted with toluene. The organic layer, dried over sodium sulfate, was evaporated, and distillation of the residue gave 6.8 g (82.9%) of product, b.p. 85° C. (0.5 mm of Hg). The thiourea derivative with aniline melted at 185°–186° C. (lit. m.p. 186°–187° C.).

Step 3: Xylazine

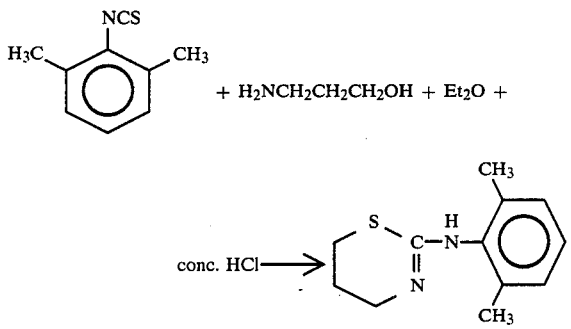

2,6-Dimethylphenylisothiocyanate (15.0 g, 0.093 mole) was added to 3-amino-1-propanol (6.9 g, 0.093 mole) in 60 ml of ether, and the mixture was heated to reflux for 0.5 hr. After the ether was evaporated, 60 ml of concentrated hydrochloric acid was added and refluxing was continued for 0.5 hr. The cooled reaction mixture was treated with 60 ml of water and filtered. The filtrate was made basic with dilute sodium hydroxide, and the precipitate was collected by filtration and washed with water. Recrystallization from ethanol-water (charcoal) gave 16.3 g (80%) of xylazine, m.p. 136°–138° C. (lit. m.p. 140°–141° C.). This step was run three times with yields ranging from 80 to 93%.

EXAMPLE II

Xylazine was prepared using a synthesis which employed Step 1 and Step 3 described in Example I. Step 2, however, employed the prior solvent system of choice, i.e. a 1:1 mixture of N,N-dimethylacetamide/benzene, as follows:

To a suspension of 2.5 g (0.05 mol) of sodium hydride in a mixture of 40 ml of dry-dimethylacetamide and 40 ml of dry benzene, 0.05 mole of N-(2,6-dimethylphenyl)acetamide was added. After evolution of hydrogen ceased, the mixture was cooled in ice and water, and with stirring 0.075 mole of carbon disulfide was added slowly. The mixture was stirred at room temperature for 20 minutes. The reaction mixture was poured into water and extracted with toluene. The organic layer, dried over sodium sulfate, was evaporated, and distillation of the residue yielded 6.1 g (74%) of 2,6-dimethylphenylisothiocyanate.

EXAMPLE III

Example II was repeated increasing the sodium hydride to 0.15 mole. The yield of 2,6-dimethylphenylisocyanate was 70%.

EXAMPLE IV

Example II was repeated increasing the reaction time from 20 minutes to 1.5 hours. The yield of 2,6-dimethylphenylisocyanate was 76%.

EXAMPLE V

Example II was repeated using a mixture of 40 ml of dimethylacetamide and 40 ml of toluene instead of the mixture of 40 ml of dimethylacetamide and 40 ml benzene. The yield of 2,6-dimethylphenylisothiocyanate was 82%. A repeat of this example yielded 85% product.

EXAMPLE VI

Example I was repeated using the solvents identified in Table 1 below in Step 2 of the synthesis and a reaction time of 30 minutes instead of 1.5 hour. The results are also reported in Table 1.

TABLE 1

| Run No. | Solvent (comments) | Wt. NCS (g) | Yield (%) |
|---|---|---|---|
| 1 | Ether (amide not soluble) | 0 | 0 |
| 2 | Ethylene glycol dimethyl ether | 4.7 | 57 |
| 3 | Tetrahydrofuran and toluene (1:1) | 1.6 | 20 |
| 4 | Tetrahydrofuran | 2.9 | 35 |

The results of the working examples demonstrate that the only solvent systems capable of achieving yields of 2,6-dimethylphenylisothiocyanate greater than 80% were tetrahydrofuran and mixtures of N,N-dimethylacetamide and toluene. Further, attempts (in Example IV) to increase yields using the prior art solvent system of choice, i.e. a 1:1 mixture of dimethylacetamide and benzene by more than quadrupaling the reaction time to 1.5 hr (vs 20 minutes) only raised the yield to 76%.

It is claimed:

1. In the preparation of 2,6-dimethylphenylisothiocyanate by reacting N-(2,6-dimethylphenyl)acetamide with sodium hydride in an organic solvent to form the corresponding anion of said amide, then reacting carbon disulfide with said anion to form said 2,6-dimethylphenylisothiocyanate, the improvement wherein the organic solvent is selected from the group consisting of tetrahydrofuran and a mixture of N,N-dimethylacetamide and toluene in a weight ratio of 1:4 to 4:1.

2. The improvement according to claim 1 wherein the organic solvent is tetrahydrofuran.

3. The improvement according to claim 1 wherein the organic solvent is a mixture of 1:4 to 4:1 N,N-dimethylacetamide and toluene.

4. The improvement according to claim 3 wherein the organic solvent is a 1:1 mixture of N,N-dimethylacetimide and toluene.

5. In the preparation of N-(2,6-Dimethylphenyl)-5,6-dihydro-4H-1,3-thiazin-2-amine by
  (i) reacting 2,6-dimethylaniline with acetic anhydride to form N-(2,6-dimethylphenyl) acetamide,
  (ii) reacting said N-(2,6-dimethylphenyl)acetamide with sodium hydride in an organic solvent to form the corresponding anion of said amide and reacting carbon disulfide with said anion to form 2,6-dimethylphenylisothiocyanate;
  (iii) reacting said 2,6-dimethylphenylisothiocyanate with 3-amino-1-propanol in a polar solvent to form the corresponding thiourea and adding concentrated hydrochloric to said thiourea and refluxing to form N-(2,6-Dimethylphenyl)-5,6-dihydro-4H-1,3-thiazin-2-amine, the improvement comprising using as the organic solvent in reaction step (ii) an organic solvent is selected from the group consisting of tetrahydrofuran and a mixture of N,N-dimethylacetimide and toluene in a weight ratio of 1:4 to 4:1.

6. The improvement according to claim 5 wherein the organic solvent is tetrahydrofuran.

7. The improvement according to claim 5 wherein the organic solvent is a mixture of N,N-dimethylacetamide and toluene in a weight ratio of 1:4 to 4:1.

8. The improvement according to claim 7 wherein the organic solvent is a 1:1 mixture of dimethylacetamide and toluene.

* * * * *